US012808973B2

(12) United States Patent
Burton et al.

(10) Patent No.: US 12,808,973 B2
(45) Date of Patent: Nov. 24, 2026

(54) DRIVER POSTURE DETECTION APPARATUS AND METHOD THEREOF

(71) Applicant: Robert Bosch GmbH, Stuttgart (DE)

(72) Inventors: Edward Burton, Clayton (AU); Traian Dumitru, Kanagawa (JP)

(73) Assignee: Robert Bosch GmbH, Stuttgart (DE)

( * ) Notice: Subject to any disclaimer, the term of this patent is extended or adjusted under 35 U.S.C. 154(b) by 225 days.

(21) Appl. No.: 18/839,905

(22) PCT Filed: Feb. 13, 2023

(86) PCT No.: PCT/IB2023/051269
§ 371 (c)(1),
(2) Date: Aug. 20, 2024

(87) PCT Pub. No.: WO2023/170487
PCT Pub. Date: Sep. 14, 2023

(65) Prior Publication Data

US 2025/0164602 A1 May 22, 2025

(30) Foreign Application Priority Data

Mar. 9, 2022 (JP) ................................. 2022-035821

(51) Int. Cl.
*G01S 5/04* (2006.01)
*A61B 5/00* (2006.01)
(Continued)

(52) U.S. Cl.
CPC .................. *G01S 5/04* (2013.01); *A61B 5/05* (2013.01); *A61B 5/1114* (2013.01);
(Continued)

(58) Field of Classification Search
CPC ... G01S 5/04; G01S 17/89; A61B 5/05; A61B 5/1114; A61B 5/1116; A61B 5/1126; A61B 5/6803; A61B 5/6806; B62J 45/00
(Continued)

(56) References Cited

U.S. PATENT DOCUMENTS 8,401,713 B2 * 3/2013 Kellum ................... G01S 11/10 700/1
8,825,086 B2 * 9/2014 Miyake .................. G01C 21/08 701/400
(Continued)

FOREIGN PATENT DOCUMENTS

JP 2017178284 A * 10/2017 .............. B62J 45/41
JP 2020158076 A * 10/2020 ............ B60W 30/09
(Continued)

OTHER PUBLICATIONS

International Search Report and Written Opinion for Application No. PCT/IB2023/051269 dated May 2, 2023 (10 pages).

*Primary Examiner* — Nuzhat Pervin
(74) *Attorney, Agent, or Firm* — Michael Best & Friedrich LLP

(57) ABSTRACT

The present invention relates to a driver posture detection apparatus and a driver posture detection method that allow a posture of a driver of a saddle-type vehicle to be detected. A driver posture detection apparatus is provided with: at least two wireless receivers that are attached to a saddle-type vehicle and each include a plurality of antennas; at least one wireless transmitter that is attached to wear of a driver of the saddle-type vehicle; a direction calculation section that calculates, based on phase information on radio waves from the wireless transmitter that are received by the wireless receiver, a direction of the wireless transmitter with respect to the wireless receiver; a position calculation section that calculates, based on direction data calculated by the direc-
(Continued)

tion calculation section, a position of the wireless transmitter with respect to the wireless receiver; and a posture calculation section that calculates, based on position data calculated by the position calculation section, a posture of the driver with respect to the saddle-type vehicle.

9 Claims, 6 Drawing Sheets

(51) Int. Cl.
*A61B 5/05* (2021.01)
*A61B 5/11* (2006.01)
*B62J 45/00* (2020.01)

(52) U.S. Cl.
CPC ........... *A61B 5/1116* (2013.01); *A61B 5/1126* (2013.01); *A61B 5/6803* (2013.01); *A61B 5/6806* (2013.01); *B62J 45/00* (2020.02)

(58) Field of Classification Search
USPC .......................................................... 342/463
See application file for complete search history.

(56) References Cited

U.S. PATENT DOCUMENTS

| | | | | |
|---|---|---|---|---|
| 9,507,023 | B2 * | 11/2016 | Nakano | G01S 15/87 |
| 9,814,051 | B1 * | 11/2017 | Shpak | H04L 27/2663 |
| 10,324,474 | B2 * | 6/2019 | Hill | G01S 5/0284 |
| 10,423,812 | B2 * | 9/2019 | Enomoto | G06K 7/10009 |
| 10,436,899 | B2 * | 10/2019 | Fukuman | G01S 15/931 |
| 10,546,501 | B2 * | 1/2020 | Berggren | G07C 5/008 |
| 10,642,560 | B2 * | 5/2020 | Hill | G01S 5/012 |
| 11,133,706 | B2 * | 9/2021 | Song | H02J 50/005 |
| 11,555,888 | B2 * | 1/2023 | Pliefke | G01S 7/40 |
| 12,374,221 | B2 * | 7/2025 | Kubo | G08G 1/123 |
| 2002/0132625 | A1 * | 9/2002 | Ogino | G01S 1/022 455/456.2 |
| 2012/0229328 | A1 * | 9/2012 | Aizawa | G01S 7/023 342/149 |
| 2014/0011540 | A1 * | 1/2014 | Miyake | G01C 5/06 455/557 |
| 2015/0002337 | A1 * | 1/2015 | Wisherd | G01S 5/0226 342/465 |
| 2016/0356883 | A1 * | 12/2016 | Sagara | G01S 7/524 |
| 2017/0020399 | A1 * | 1/2017 | Shemesh | A61B 5/0205 |
| 2018/0070850 | A1 * | 3/2018 | Stafford | A61B 5/16 |
| 2018/0260593 | A1 * | 9/2018 | Enomoto | G06K 7/10435 |
| 2020/0011986 | A1 * | 1/2020 | Yamanouchi | G01S 13/42 |
| 2020/0064444 | A1 * | 2/2020 | Regani | G01S 7/006 |
| 2021/0188311 | A1 * | 6/2021 | Cho | H04W 72/23 |
| 2022/0126690 | A1 * | 4/2022 | Maeda | B60K 35/215 |
| 2022/0161804 | A1 * | 5/2022 | Fujimoto | B60W 30/08 |
| 2022/0402488 | A1 * | 12/2022 | Fujimoto | B62J 45/41 |
| 2023/0202594 | A1 * | 6/2023 | Hara | B62J 1/28 701/36 |
| 2023/0242114 | A1 * | 8/2023 | Matsumoto | B60W 30/165 701/96 |

FOREIGN PATENT DOCUMENTS

| | | | | |
|---|---|---|---|---|
| JP | 7012806 | B1 * | 1/2022 | H04W 4/40 |
| WO | WO-2015064246 | A1 * | 5/2015 | B62J 45/00 |
| WO | WO-2019113441 | A1 * | 6/2019 | A61B 5/1114 |

* cited by examiner

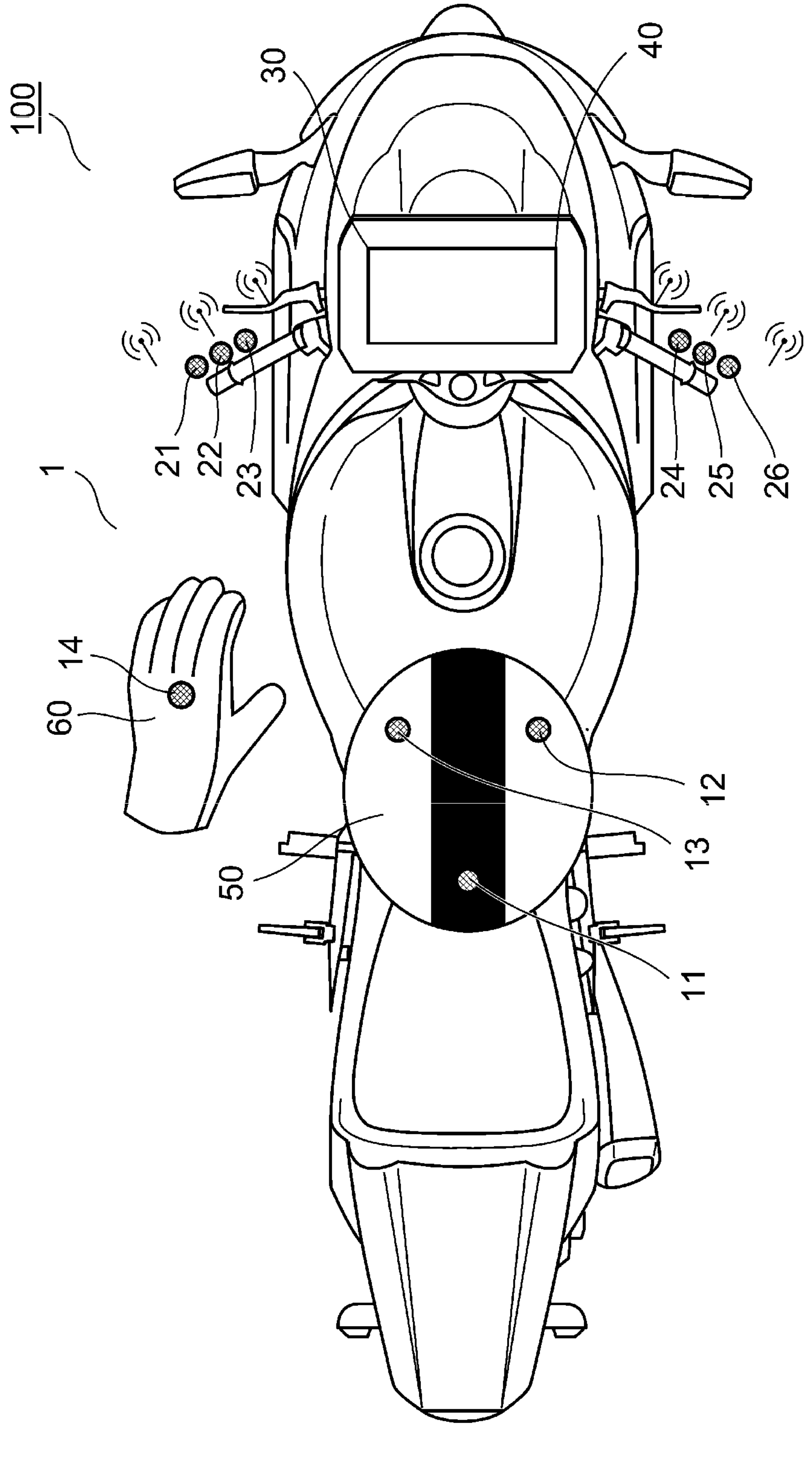
[FIG. 1]

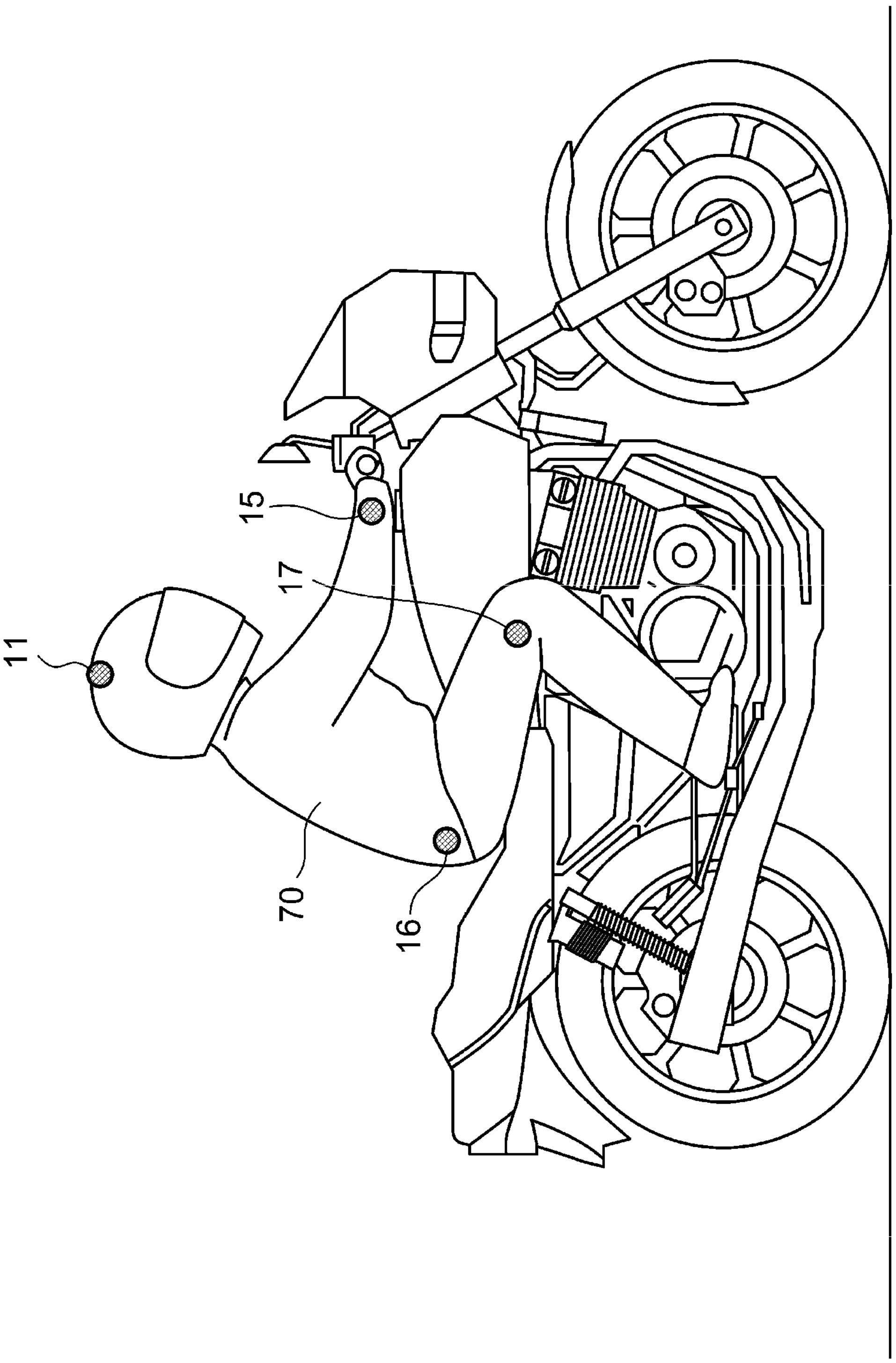
[FIG. 2]

[FIG. 3]
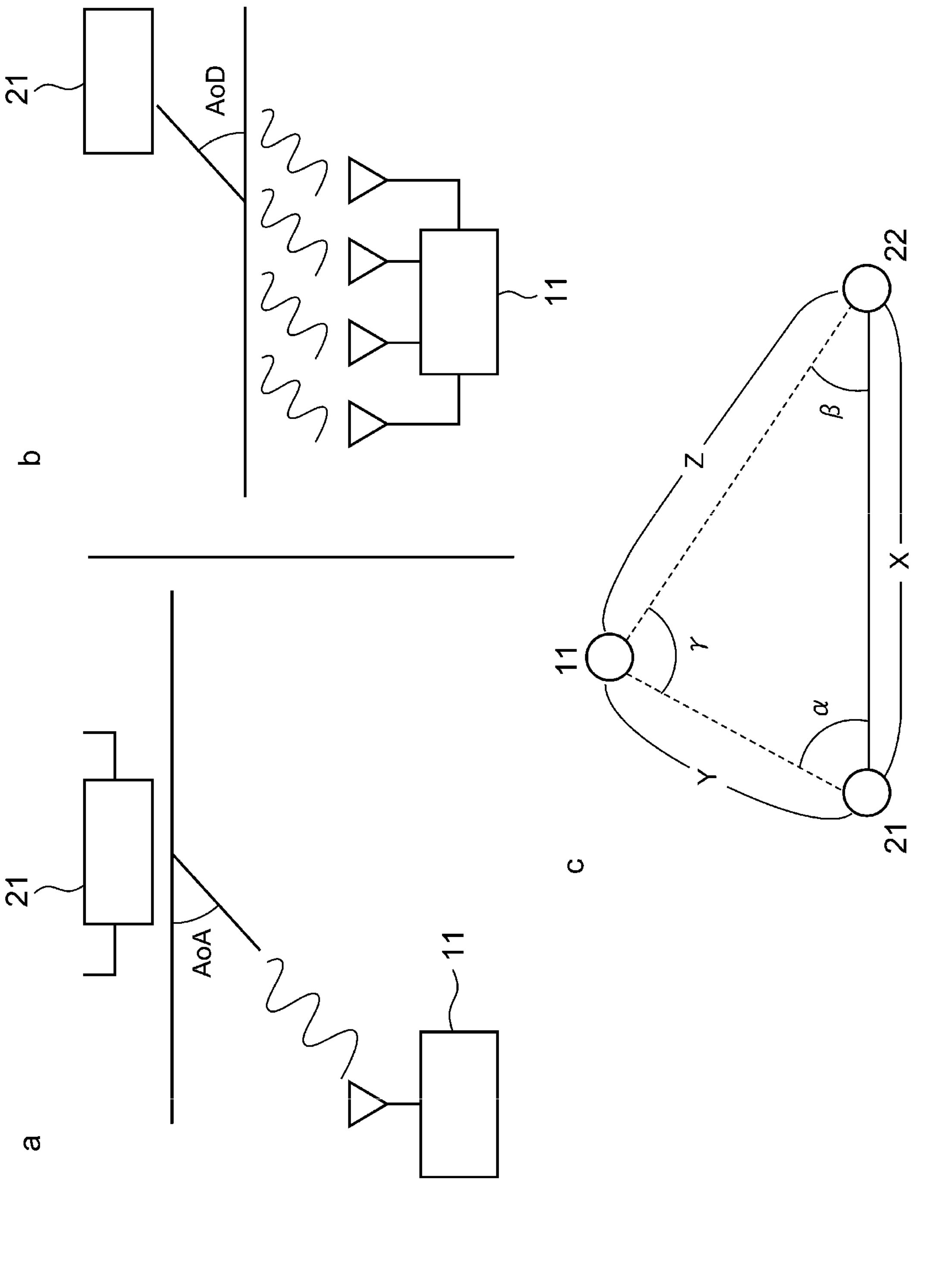

[FIG. 4]
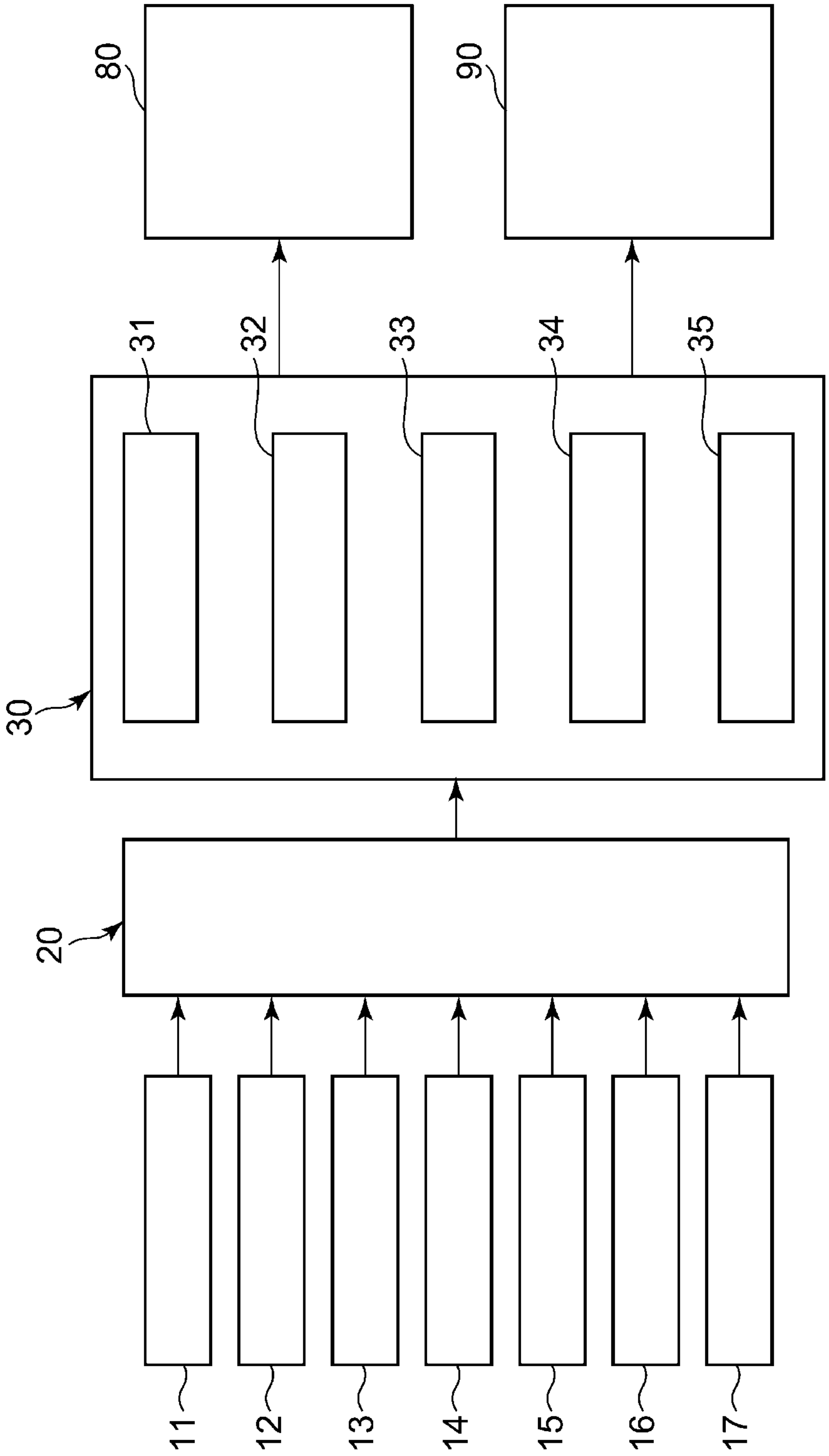

[FIG. 5]
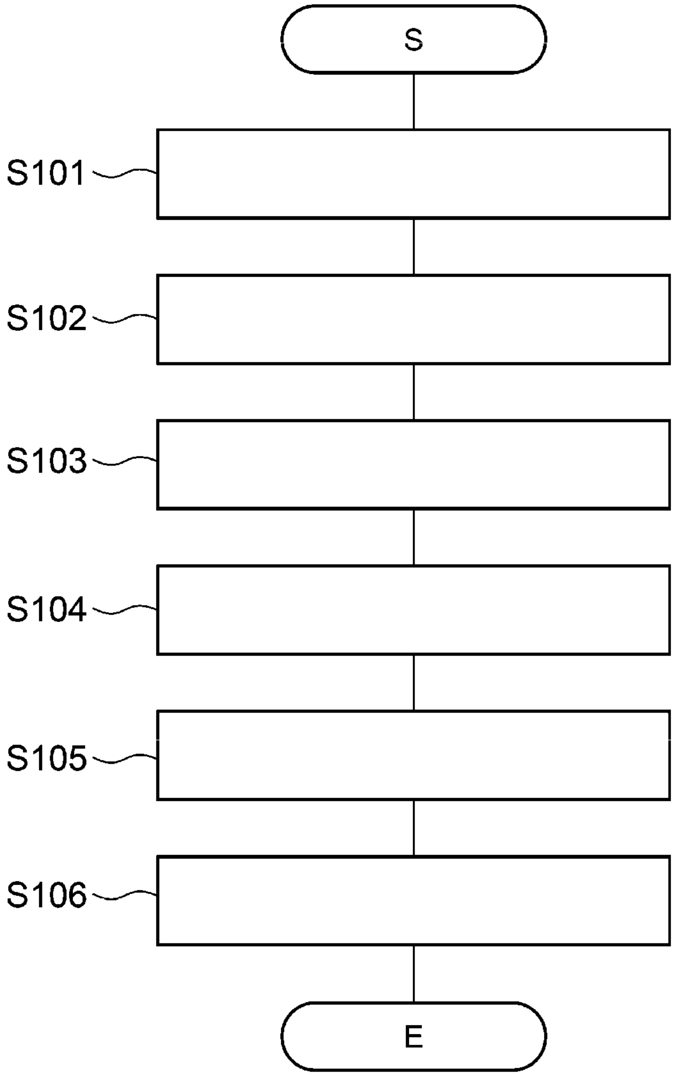

[FIG. 6]
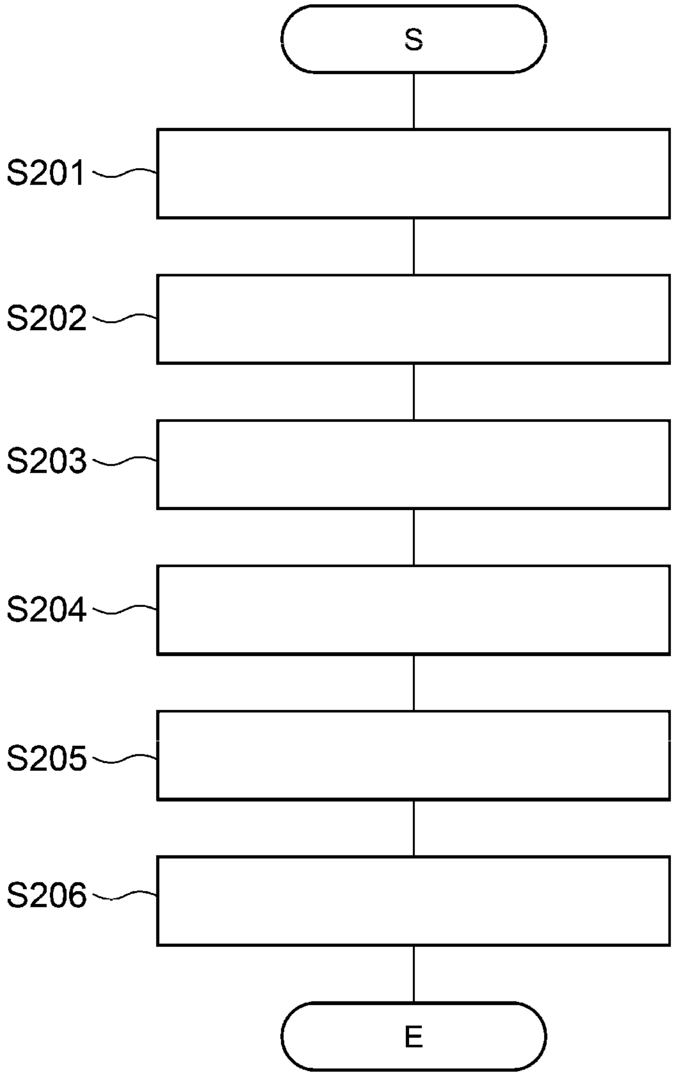

DRIVER POSTURE DETECTION APPARATUS AND METHOD THEREOF

BACKGROUND

The present invention relates to a driver posture detection apparatus and a driver posture detection method capable of detecting various postures of a driver using wireless communication apparatuses that are attached to wear of the driver and a saddle-type vehicle.

As techniques to be applied to saddle-type vehicles (for example, a two-wheeled motor vehicle, a bicycle, and the like), a technique is known in which a communication apparatus including a handle grip site and the like that are directly touched by a driver within a communication possible range and an NFC communication apparatus that is provided to a glove that the driver wears communicate with each other, whereby electric power is supplied to the NFC communication apparatus in a non-contact manner (for example, see WO2015/064246A1).

With this technique, it is possible to store data transferred from a mobile terminal in a memory via the NFC communication apparatus, and take in setting values to be used for various kinds of control of the two-wheeled motor vehicle from the mobile terminal based on the stored data.

However, with the communication technique, a contact state between the driver and the vehicle can be determined, but a posture of the driver in the vehicle cannot be determined.

Specially, the weight rate of the driver relative to a vehicle weight in a saddle-type vehicle such as a two-wheeled motor vehicle is larger than that in a four-wheel automobile and the like, so that a vehicle body behavior during driving largely depends on the posture of the driver. Therefore, a wireless communication technique for determining a posture of a driver in a vehicle, and applying results thereof to various kinds of control of the vehicle, has been desired.

SUMMARY

The invention is made in view of the abovementioned problems, and provides a driver posture detection apparatus and a driver posture detection method capable of detecting a posture of a driver in a saddle-type vehicle with the high accuracy and with the reduced electric power consumption.

A driver posture detection apparatus according to the invention is provided with: at least two wireless receivers that are attached to a saddle-type vehicle and each include a plurality of antennas; at least one wireless transmitter that is attached to wear of a driver of the saddle-type vehicle; a direction calculation section that calculates, based on phase information on radio waves from the wireless transmitter that are received by the wireless receiver, a direction of the wireless transmitter with respect to the wireless receiver; a position calculation section that calculates, based on direction data calculated by the direction calculation section, a position of the wireless transmitter with respect to the wireless receiver; and a posture calculation section that calculates, based on position data calculated by the position calculation section, a posture of the driver with respect to the saddle-type vehicle.

Moreover, a driver posture detection apparatus according to the invention is provided with: at least one wireless receiver that is attached to a saddle-type vehicle; at least two wireless transmitters that are attached to wear of a driver of the saddle-type vehicle and each include a plurality of antennas; a direction calculation section that calculates, based on phase information on radio waves from the wireless transmitter that are received by the wireless receiver, a direction of the wireless transmitter with respect to the wireless receiver; a position calculation section that calculates, based on direction data calculated by the direction calculation section, a position of the wireless transmitter with respect to the wireless receiver; and a posture calculation section that calculates, based on position data calculated by the position calculation section, a posture of the driver with respect to the saddle-type vehicle.

Moreover, a driver posture detection method according to the invention is a driver posture detection method that detects a posture of a driver who gets on a saddle-type vehicle, and includes: a transmission step of transmitting unmodulated radio waves during a fixed period from a wireless transmitter that is attached to wear of the driver of the saddle-type vehicle; a reception step of receiving the unmodulated radio waves in at least two wireless receivers that are attached to the saddle-type vehicle and each include a plurality of antennas; a direction calculation step of calculating, based on phase information on the radio waves from the wireless transmitter that are received by the wireless receiver, a direction of the wireless transmitter with respect to the wireless receiver; a position calculation step of calculating, based on direction data calculated at the direction calculation step, a position of the wireless transmitter with respect to the wireless receiver; and a posture calculation step of calculating, based on position data calculated at the position calculation step, a posture of the driver with respect to the saddle-type vehicle.

Moreover, the driver posture detection method according to the invention is a driver posture detection method that detects a posture of a driver who gets on a saddle-type vehicle, and includes: a transmission step of transmitting unmodulated radio waves during a fixed period from at least two wireless transmitters that are attached to wear of the driver and each include a plurality of antennas; a reception step of receiving the unmodulated radio waves in a wireless receiver that is attached to the saddle-type vehicle; a direction calculation step of calculating, based on phase information on the radio waves from the wireless transmitter that are received by the wireless receiver, a direction of the wireless transmitter with respect to the wireless receiver; a position calculation step of calculating, based on direction data calculated at the direction calculation step, a position of the wireless transmitter with respect to the wireless receiver; and a posture calculation step of calculating, based on position data calculated at the position calculation step, a posture of the driver with respect to the saddle-type vehicle.

Advantageous Effects of Invention

With the driver posture detection apparatus according to the invention and the method thereof, it is possible to calculate, based on phase information on radio waves from a wireless transmitter that are received by a wireless receiver, a direction of the wireless transmitter with respect to the wireless receiver, and calculate a posture of a driver with respect to a saddle-type vehicle, based on position data calculated based on the direction data. Therefore, it is possible to detect the posture of the driver with respect to the saddle-type vehicle with the high accuracy and with the reduced electric power consumption.

BRIEF DESCRIPTION OF THE DRAWINGS

FIG. 1 is a diagram illustrating one example of a mounted state of a driver posture detection apparatus according to the invention to a two-wheeled motor vehicle.

FIG. 2 is a diagram illustrating one example of an arrangement of wireless transmitters in wear of a driver in the driver posture detection apparatus according to the invention.

FIG. 3 illustrates diagrams of a mechanism of calculating a position of the wireless transmitter with respect to a wireless receiver in the driver posture detection apparatus according to the invention.

FIG. 4 is a diagram illustrating a system configuration of the driver posture detection apparatus according to the invention.

FIG. 5 is a diagram illustrating an operation flow of a processing unit in the driver posture detection apparatus according to a first embodiment of the invention.

FIG. 6 is a diagram illustrating an operation flow of the processing unit in the driver posture detection apparatus according to a second embodiment of the invention.

DETAILED DESCRIPTION

A driver posture detection apparatus and a driver posture detection method according to the invention will be described with reference to the drawings below.

Note that, the configuration, the operation, and the like to be described below are examples, and the driver posture detection apparatus according to the invention is not limited to that having such the configuration, the operation, and the like.

For example, a case where a saddle-type vehicle is a two-wheeled motor vehicle is described below, but the saddle-type vehicle may be a bicycle or a three-wheeled motor vehicle.

Moreover, the same or similar descriptions are simplified or omitted as appropriate below. Moreover, the same or similar portions are denoted with the same reference numerals in the respective drawings. Moreover, detailed structures are simplified or omitted as appropriate.

A driver posture detection apparatus 1 will be described below.

<Configuration of Driver Posture Detection Apparatus>

A configuration of the driver posture detection apparatus 1 will be described.

FIG. 1 is a diagram illustrating a mounted state of the driver posture detection apparatus 1 according to the invention to a two-wheeled motor vehicle.

As illustrated in FIGS. 1 and 2, the driver posture detection apparatus 1 includes wireless receivers 21, 22, 23, 24, 25, and 26 that are mounted to a two-wheeled motor vehicle 100, wireless transmitters 11, 12, 13, 14, 15, 16, and 17 that are attached to wear of a driver, and a processing unit 30. FIG. 1 is a diagram of the two-wheeled motor vehicle 100 seen from the upper side, and FIG. 2 is a diagram of the two-wheeled motor vehicle 100 seen from the side.

In a case where a reception angle (AoA: Angle of Arrival) is employed as a method of detecting a direction, an antenna array with which a plurality (two at the minimum) of antennas are equipped is attached to each of the wireless receivers 21, 22, 23, 24, 25, and 26. A predetermined distance is present between the respective antennas of the wireless receiver, so that the wireless receiver can receive signals having different phases, whereby an angle can be calculated from a phase difference.

In contrast, in a case where an emission angle (AoD: Angle of Departure) is employed as a method of detecting a direction, each of the wireless receivers 21, 22, 23, 24, 25, and 26 is equipped with a single antenna, and an antenna array with which a plurality of antennas are equipped is attached to each of the wireless transmitters 11, 12, 13, 14, 15, 16, and 17 in this case.

For example, Bluetooth (registered trademark) Low Energy (BLE) is applied to a wireless apparatus including a wireless receiver and a wireless transmitter and having a direction finding extended function that enables position tracking. At least either one of the wireless receiver and the wireless transmitter includes a plurality of antennas, at least two or more antennas, and determines a direction of the wireless transmitter based on a phase difference in radio waves that are received between the different antennas.

An identification method of a position of the wireless transmitter using BLE or the like with respect to the wireless receiver will be described in detail later.

In the example of FIG. 1, the three wireless receivers 21, 22, and 23 and the three wireless receivers 24, 25, and 26 are arranged respectively at equal intervals to a left grip portion of a handlebar and a right grip portion of the handlebar. The positions of the wireless receivers 21, 22, 23, 24, 25, and 26 in the two-wheeled motor vehicle 100 are stored in advance in a storage section 35 of the processing unit 30. Note that, the positions of the wireless receivers are not limited to the grip portions, but the wireless receivers may be arranged to another location, for example, an inside of a cluster panel 40, as long as the wireless receivers are fixed to the two-wheeled motor vehicle 100 at the positions.

The wireless transmitters 11, 12, and 13 are arranged to a helmet that the driver wears. In the example of FIG. 1, the wireless transmitters 12 and 13 are symmetrically arranged to a front portion of the helmet, and the wireless transmitter 11 is arranged in a rear center portion of the helmet. The positions of the wireless transmitters 11, 12, and 13 are not limited to the positions illustrated in FIG. 1, but at least the two or more wireless transmitters are preferably symmetrically arranged in order to identify a line-of-sight direction of the driver.

Moreover, the wireless transmitter 14 is attached to a glove 60 that the driver wears, and is arranged to a portion corresponding to a back of a hand of the driver in the example of FIG. 1.

In addition, the wireless transmitters 15, 16, and 17 are arranged to a rider suit that the driver wears, and are arranged to portions corresponding to a wrist, a knee, and a lower back of the driver in the example of FIG. 2. The identification of whether the driver grips the handle, straddles a seat with the both of left and right knees, and sits down on the seat has a large effect on the calculation of a position of the center of gravity of the driver, so that the wireless transmitters 15, 16, and 17 are preferably arranged to the locations of the rider suit corresponding to the wrist, the knee, and the lower back of the driver.

Next, with reference to FIG. 3, a mechanism of direction calculation by the wireless apparatus including the wireless receiver and the wireless transmitter, and a calculation method of a distance between the wireless receiver and the wireless transmitter will be described in detail.

As methods of direction detection, a direction of a signal can be identified with two types of methods of the reception angle (AoA: Angle of Arrival) and the emission angle (AoD: Angle of Departure). In both of AoA and AoD, an antenna array including a plurality of antennas is necessary.

In the method of AoA in FIG. 3*a*, a device (in other words, the wireless transmitter 11) a direction of which is to be identified transmits an unmodulated radio wave from a single antenna, like a tag in a real-time location system (RTLS) solution. A plurality of antennas need to be arranged to the wireless receiver 21, like locators in the RTLS solution.

A direction calculation section 31 calculates a relative direction of the signal based on the IQ sample.

Distances between the single antenna of the wireless transmitter 11 and the plurality of the antennas of the wireless receiver 21 are different from one another, so that when signals transmitted from the single antenna of the wireless transmitter 11 have reached the plurality of the antennas of the wireless receiver 21, the wireless receiver 21 detects signals having different phases for the respective antennas. The wireless receiver 21 acquires in-phase and quadrature-phase (IQ) samples while switching the active antenna.

In the method of AoD in FIG. 3*b*, a device (in other words, the wireless transmitter 11) a direction of which is to be identified transmits unmodulated radio waves from the antenna array in which a plurality of antennas are disposed, like locator beacons in an indoor positioning system (IPS) solution. The wireless receiver 21 needs a single antenna, like a mobile telephone in the IPS solution.

When the radio waves transmitted from the plurality of the antennas of the wireless transmitter 11 have reached the single antenna of the wireless receiver 21, the wireless receiver 21 acquires IQ samples. The direction calculation section 31 calculates a relative direction of the signal based on the IQ sample.

In the direction detection function, an antenna array including a plurality of antennas is used, and phase information on the radio waves due to the different locations of the antennas is used, thereby detecting an incoming direction of the radio waves. The antenna array is connected to the respective antennas from one BLE device via RF switches, and is used by switching the switches at high speed within a fixed period in the direction detection.

A special mechanism is necessary for the direction detection because the radio waves to be used for normal communication are modulated for transmission of digital data, and the phase changes all the time. In order to send monotonous sine waves, the wireless transmitter 11 allows herein the unmodulated radio wave transmission as Constant Tone Extension (CTE) during a fixed period immediately after having performed the normal data communication.

A method in which the CTE is received by the antenna array of the wireless receiver 21 to calculate an incident angle is AoA, and a method in which the CTE is output from the antenna array of the wireless transmitter 11 and a phase difference in the CTE to be reached to the wireless receiver including a single antenna is calculated to obtain an angle is AoD.

After the angle of the wireless transmitter 11 with respect to the wireless receiver 21 has been calculated by AoA or AoD, a distance Y between the wireless transmitter 11 and the wireless receiver 21 needs to be calculated. The calculation method will be described with reference to FIG. 3*c*. In FIG. 3*c*, a calculation method of a distance between the wireless receiver 21 and the wireless transmitter 11 and a distance between the wireless receiver 22 and the wireless transmitter 11 will be described, in a case where the angle has been calculated by AoA.

The wireless receiver 21 and the wireless receiver 22 are arranged at arbitrary positions as in FIG. 1, and a distance X between the wireless receivers is thus stored in advance in the storage section 35. When radio waves from the wireless transmitter 11 are received, an angle $\alpha$ of the wireless transmitter 11 with respect to the wireless receiver 21 and an angle $\beta$ of the wireless transmitter 11 with respect to the wireless receiver 22 are obtained by the previously mentioned AoA, and an angle of an angle $\gamma$ can be obtained ($\alpha+\beta+\gamma=180°$). Accordingly, the distances Y and Z from the wireless receivers 21 and 22 to the wireless transmitter 11 can be obtained by the following sine theorem.

$$Z/\sin\alpha = Y/\sin\beta = X/\sin\gamma.$$

In this manner, the directions and the distances of the wireless transmitter 11 with respect to the wireless receivers 21 and 22 are calculated to identify a position of the wireless transmitter 11 with respect to the wireless receivers 21 and 22.

Next, with reference to FIG. 4, a system configuration of the driver posture detection apparatus 1 will be described.

The processing unit 30 at least includes the direction calculation section 31, a position calculation section 32, a posture calculation section 33, a communication section 34, and the storage section 35. The respective sections of the processing unit 30 may be collectively provided to one housing, or may be separately provided to a plurality of housings. Moreover, a part or all of the processing unit 30 may include, for example, a microcomputer, a microprocessor unit, and the like, may include an updatable component such as firmware, and may be a program module or the like that is executed by a command from the CPU or the like.

The direction calculation section 31 acquires phase information, and calculates a direction of the wireless transmitter with respect to the wireless receiver. The antennas of the respective wireless receivers are switched to calculate a phase difference for each antenna in AoA, and timing is cut out from the received signal based on the sent antenna pattern and the timing information to calculate a phase difference in AoD. In a case where three or more antennas are present, the accuracy of the direction calculation can be improved by performing the similar calculation with respect to the plurality of the antennas on the antenna array.

The position calculation section 32 calculates a distance between the wireless transmitter and the wireless receiver from the sine theorem based on direction data calculated by the direction calculation section 31, and calculates a position of the wireless transmitter with respect to the wireless receiver. Similar to the direction calculation section 31, in a case where three or more antennas are present, the accuracy of the position calculation can be improved by performing the similar calculation with respect to the plurality of the antennas on the antenna array.

The posture calculation section 33 inputs position data calculated by the position calculation section 32 to a posture determination model stored in the storage section 35, thereby calculating a posture of the driver with respect to the two-wheeled motor vehicle 100.

Specifically, the posture calculation section 33 inputs position information on each of the wireless transmitters 11, 12, and 13 that are attached to the helmet with respect to at least one of the wireless receivers 21, 22, 23, 24, 25, and 26 into a posture determination model, and identifies a line-of-sight direction of the driver from output of the posture determination model.

In other words, the posture determination model includes an information output function for determining, for example, whether the driver faces forward or rearward relative to the two-wheeled motor vehicle 100, from the combination of the positions to be input of the wireless transmitters 11, 12, and 13.

Note that, the accuracy of the posture determination model may be improved by causing the posture determination model to perform machine learning with input of position information on the wireless transmitter.

Moreover, as another concrete example, the posture calculation section 33 inputs position information on the wireless transmitter 14 that is attached to the glove of the driver with respect to at least one of the wireless receivers 21, 22, 23, 24, 25, and 26 into a posture determination model, and calculates a state of handle gripping by the driver from output of the posture determination model.

In other words, the posture determination model includes herein an information output function of determining whether the driver grips the handle from the position to be input of the wireless transmitter 14 with respect to any of the wireless receivers.

As still another concrete example, from position information on the wireless transmitters 11, 12, and 13 that are attached to the helmet and the wireless transmitters 15, 16, and 17 that are attached to the rider suit of the driver with respect to at least one of the wireless receivers 21, 22, 23, 24, 25, and 26, a position of the center of gravity of the driver may be calculated using the posture determination model.

The communication section 34 transmits posture information on the driver calculated by the posture calculation section 33 to various kinds of vehicle control systems. In a case where the posture calculated by the posture calculation section 33 is a line-of-sight direction of the driver, the communication section 34 can transmit the posture information to a driving assist system 80. When the posture calculation section 33 recognizes that the line-of-sight of the driver indicates rearward of the two-wheeled motor vehicle 100, for example, the communication section 34 may transmit the information to the driving assist system 80 to cause a lane change assist system that is one function of the driving assist system to automatically operate.

In a case where the posture calculated by the posture calculation section 33 has been a gripping state of the handle by the driver, the communication section 34 can transmit the posture information to the driving assist system 80. When the posture calculation section 33 recognizes that the driver performs traveling without gripping the handle, for example, the communication section 34 transmits the information to the driving assist system 80 to allow warning to the driver to be issued from a warning system that is one function of the driving assist system.

In a case where the posture calculated by the posture calculation section 33 has been a position of the center of gravity of the driver with respect to the two-wheeled motor vehicle 100, the communication section 34 can transmit the posture information to a brake control system 90. Therefore, a brake control function for vehicle stability in which the position of the center of gravity of the driver is considered can be caused to operate.

<Operation of Driver Posture Detection Apparatus>

An operation of a driver posture detection apparatus according to a first embodiment will be described.

FIG. 5 is a diagram illustrating an operation flow of the driver posture detection apparatus according to the first embodiment of the invention.

The driver posture detection apparatus 1 executes the operation flow illustrated in FIG. 5. Note that, the embodiment according to FIG. 5 is based on the incident angle calculation method by AoA.

(Transmission Step of Radio Wave by Wireless Transmitter)

At Step S101, the wireless transmitter performs the unmodulated radio wave transmission as Constant Tone Extension (CTE) during a fixed period after having performed the normal data communication.

(Reception Step of Radio Wave by Wireless Receiver)

At Step S102, a wireless receiver including a plurality of antennas receives unmodulated radio waves as CTE during a fixed period from the wireless transmitter.

(Direction Calculation Step of Wireless Transmitter by Direction Calculation Unit)

At Step S103, the direction calculation section calculates an incident angle based on a phase difference in radio waves for each antenna from CTE that is received by the plurality of the antennas of the wireless receiver, in other words, a direction of the wireless transmitter with respect to the wireless receiver.

(Position Calculation Step of Wireless Transmitter by Position Calculation Unit)

At Step S104, the position calculation section calculates a distance between the wireless transmitter and the wireless receiver based on the direction of the wireless transmitter calculated at the direction calculation step S103. Accordingly, the direction of the wireless transmitter with respect to the wireless receiver and the distance between the wireless transmitter and the wireless receiver are calculated, so that a position of the wireless transmitter with respect to the wireless receiver is determined.

(Driver's Posture Calculation Step by Posture Calculation Unit)

At Step S105, the posture calculation section inputs position information on the wireless transmitter with respect to the wireless receiver calculated at the position calculation step S104 into a posture determination model, thereby calculating a posture of the driver with respect to the vehicle.

At Step S106, the communication section 34 transmits posture information on the driver with respect to the vehicle calculated at the posture calculation step S105 to various kinds of the vehicle control systems.

<Effects by Driver Posture Detection Apparatus>

Effects by the driver posture detection apparatus according to the first embodiment will be described.

With the first embodiment, a direction of the wireless transmitter with respect to the wireless receiver is calculated by AoA. Therefore, it is possible to accurately calculate a position of the wireless transmitter with respect to the wireless receiver with the reduced electric power consumption. Moreover, specially, in a case of AoA, the wireless transmitter to be attached to the wear of the driver is the wireless transmitter including a single antenna and having comparatively reduced electric power consumption, so that it is possible to reduce a power supply load of a power supply that is attached to the wear of the driver.

Next, an operation of a driver posture detection apparatus according to a second embodiment will be described.

The driver posture detection apparatus 1 executes an operation flow illustrated in FIG. 6. Note that, the embodiment according to FIG. 6 is based on the emission angle calculation method by AoD.

(Transmission Step of Radio Wave by Wireless Transmitter)

At Step S201, the wireless transmitter performs the unmodulated radio wave transmission as Constant Tone Extension (CTE) during a fixed period after having performed the normal data communication.

(Reception Step of Radio Wave by Wireless Receiver)

At Step S202, the wireless receiver including a single antenna receives unmodulated radio waves as CTE during a fixed period, while receiving radio waves from the wireless transmitter that are transmitted by a plurality of antennas.

(Direction Calculation Step of Wireless Transmitter by Direction Calculation Unit)

At Step S203, the direction calculation section calculates an emission angle based on a phase difference from the respective antennas of the wireless transmitter that are received by the single antenna of the wireless receiver, in other words, a direction of the wireless transmitter with respect to the wireless receiver.

(Position Calculation Step of Wireless Transmitter by Position Calculation Unit)

At Step S204, the position calculation section calculates a distance between the wireless transmitter and the wireless receiver based on the direction of the wireless transmitter calculated at the direction calculation step S103. Accordingly, the direction of the wireless transmitter with respect to the wireless receiver and the distance between the wireless transmitter and the wireless receiver are calculated, so that a position of the wireless transmitter with respect to the wireless receiver is determined.

(Driver's Posture Calculation Step by Posture Calculation Unit)

At Step S205, the posture calculation section inputs position information on the wireless transmitter with respect to the wireless receiver calculated at the position calculation step S204 into a posture determination model, thereby calculating a posture of the driver with respect to the vehicle.

At Step S206, the communication section 34 transmits posture information on the driver with respect to the vehicle calculated at the posture calculation step S205 to various kinds of the vehicle control systems.

<Effect by Driver Posture Detection Apparatus>

Effects by the driver posture detection apparatus according to the second embodiment will be described.

With the second embodiment, a direction of the wireless transmitter with respect to the wireless receiver is calculated by AoD. Therefore, similar to the case of AoA, it is possible to accurately calculate a position of the wireless transmitter with respect to the wireless receiver with the reduced electric power consumption, and to provide a position calculation option other than AoA.

In the foregoing, the first and second embodiments have been described, however, the invention is not limited to the description about the respective embodiments. For example, the operations of the respective steps may be performed in a time-series manner, which has been described, or a part of the steps may be simultaneously executed.

REFERENCE SIGNS LIST

1: Driver posture detection apparatus
11 to 17: Wireless transmitter
21 to 26: Wireless receiver
30: Processing unit
31: Direction calculation section
32: Position calculation section
33: Posture calculation section
34: Communication section
35: Storage section
40: Cluster panel
60: Glove
80: Driving assist system
90: Brake control system
100: Two-wheeled motor vehicle

The invention claimed is:

1. A driver posture detection apparatus comprising:

at least two wireless receivers that are attached to a saddle-type vehicle and each include a plurality of antennas;

at least one wireless transmitter that is attached to wear of a driver of the saddle-type vehicle and includes a single antenna;

a direction calculation section that calculates, based on phase information on radio waves from the wireless transmitter that are received by the wireless receiver, a direction of the wireless transmitter with respect to the wireless receiver;

a position calculation section that calculates, based on direction data calculated by the direction calculation section, a position of the wireless transmitter with respect to the wireless receiver;

a posture calculation section that calculates, based on position data calculated by the position calculation section, a posture of the driver with respect to the saddle-type vehicle; and a communication section, wherein the posture calculation section calculates a line-of-sight direction of the driver as posture information, and wherein the communication section transmits the posture information to a driving assistance system that automatically operates a lane change assistance function based on the posture information.

2. The driver posture detection apparatus according to claim 1, further comprising a storage section that stores therein a posture determination model, wherein the posture calculation section inputs the position data calculated by the position calculation section into the posture determination model to calculate the posture of the driver.

3. The driver posture detection apparatus according to claim 1, wherein the wireless transmitter is attached to a helmet that the driver wears.

4. The driver posture detection apparatus according to claim 1, wherein the wireless transmitter is attached to a glove that the driver wears.

5. The driver posture detection apparatus according to claim 4, wherein the posture calculation section calculates a gripping state of a handle by the driver.

6. The driver posture detection apparatus according to claim 1, wherein the wireless transmitter is further attached to a rider suit that the driver wears.

7. The driver posture detection apparatus according to claim 6, wherein the posture calculation section calculates a position of a center of gravity of the driver with respect to the saddle-type vehicle.

8. The driver posture detection apparatus according to claim 1, wherein the wireless receiver is attached to a handlebar.

9. A driver posture detection method that detects a posture of a driver who gets on a saddle-type vehicle, the driver posture detection method comprising:

a transmission step of transmitting unmodulated radio waves during a fixed period from a wireless transmitter that is attached to wear of the driver and includes a single antenna;

a reception step of receiving the unmodulated radio waves in at least two wireless receivers that are attached to the saddle-type vehicle and each include a plurality of antennas;

a direction calculation step of calculating, based on phase information on the radio waves received by the wireless receiver from the wireless transmitter, a direction of the wireless transmitter with respect to the wireless receiver;

a position calculation step of calculating, based on direction data calculated at the direction calculation step, a position of the wireless transmitter with respect to the wireless receiver;

a posture calculation step of calculating, based on position data calculated at the position calculation step, a posture of the driver with respect to the saddle-type vehicle and a line-of-sight direction of the driver as posture information; and a communication step, wherein a communication section transmits the posture information to a driving assistance system that automatically operates a lane change assistance function based on the posture information.

* * * * *